(12) United States Patent
Stephan et al.

(10) Patent No.: US 8,299,284 B2
(45) Date of Patent: Oct. 30, 2012

(54) FRUSTRATED LEWIS PAIR COMPOSITIONS

(75) Inventors: Douglas W. Stephan, Toronto (CA); Preston A. Chase, Kingston (CA); Gregory C. Welch, Santa Barbara, CA (US)

(73) Assignee: Stephan Consulting Corporation, Toronto, Ontario (CA)

( * ) Notice: Subject to any disclaimer, the term of this patent is extended or adjusted under 35 U.S.C. 154(b) by 556 days.

(21) Appl. No.: 12/514,901

(22) PCT Filed: Nov. 14, 2007

(86) PCT No.: PCT/IB2007/004577
§ 371 (c)(1),
(2), (4) Date: May 14, 2009

(87) PCT Pub. No.: WO2008/125911
PCT Pub. Date: Oct. 23, 2008

(65) Prior Publication Data
US 2010/0048949 A1    Feb. 25, 2010

Related U.S. Application Data

(60) Provisional application No. 60/865,684, filed on Nov. 14, 2006, provisional application No. 60/896,557, filed on Mar. 23, 2007.

(51) Int. Cl.
C07F 7/00    (2006.01)
C07F 5/06    (2006.01)
C07F 9/00    (2006.01)

(52) U.S. Cl. .................. 556/23; 556/1; 556/20; 556/52; 556/172; 556/174

(58) Field of Classification Search .................. 556/172, 556/174, 1, 20, 23, 52; 564/8, 489; 568/2, 568/881
See application file for complete search history.

(56) References Cited

U.S. PATENT DOCUMENTS
2001/0049331 A1    12/2001    Chang

FOREIGN PATENT DOCUMENTS
WO    2004113351    12/2004

OTHER PUBLICATIONS

Kuroboshi et al., Bull. Chem. Soc. Jpn., vol. 63, No. 4, pp. 1191-1195 (1990).*
Bai, Guangcai, et al., "Formation of C-C and C-N Bonds in Ni Ketimide Complexes via Transient Ni Aryl Imides"; interScience; Angew. Chem. Int. Ed. 2007, 46, 1856-1859.
Chase, Preston A., et al., "Metal-Free Cataalytic Hydrogenation"; Angew. Chem. Int. Ed. 2007, 46, 1-5.
Welch, Gregory C., et al., "Tuning Lewis acidity using the reactivity of "frustrated Lewis pairs": facile formation of phosphine-boranes and cationic phosphonium-boranes"; The Royal Society of Chemistry 2007; Dalton Trans., 2007, 3407-3414.
Welch, Gregory C., et al., "Phosphonium-Borate Zwitterions, Anionic Phosphines, and Dianionic Phosphonium-Dialkoxides via Tetrahydrofuran Ring-Opening Reactions"; Inorganic Chemistry, vol. 45, No. 2, 2006; pp. 478-480.
Cabrera, Lourdes, et al., Pyridine and phosphine reactions with [CPh3][B9C6F5)4]; Inorganica Chimica Acta; Elsevier, (2006).
Welch, Gregory C., et al., "Reversible, Metal-Free Hydrogen Activation"; Science Nov. 17, 2006: vol. 314; No. 5802; pp. 1124-1126.
Welch, Gregory C., et al., "Facile Heterolytic Cleavage of Dihydrogen by Phosphines and Boranes"; 1880; J. Am. Chem. Soc. 2007, 129, 1880-1881.
Welch, Gregory C., et al., "Reversible, Metal-Free Hydrogen Activation"; Nov. 17, 2006; vol. 314, Science; www.sciencemag.org.
Kubas, Greogry J. et al., "Chemistry: Breaking the H2 Marriage and Reuniting the Couple"; Science 314, 1096 (2006).
Chase, Preston A., et al., "Metal-Free Catalytic Hydrogenation", Communications, Angew, Chem, Int. Ed. 2007, 46, 8050-8053.
Communications, Inorganic Chemistry, vol. 45, No. 2., 2006, pp. 479-480. Welch, Gregory C., et al., "Phosphonium-Borate Zwitterions, Anionic Phosphines and Dianionic-Phosphonium-Dialkoxides via THF Ring Opening Reactions", (2006).
Berkessel, Albrecht, et al., "Hydrogenation without a Transition-Metal Catalyst: On the Mechanism of the Base-Catalyzed Hdrogenation of Ketones", J.Am.Chem. Soc. 2002, 124, 8693-8698.
Welch, Gregory C., et al., "Reversible, Metal-Free Hydrogen Activation", Science Nov. 17, 2006, vol. 314, No. 5802, pp. 1124-1126.
Spies, P., et al., "Rapid Intramolecular Heterolytic Dihydrogen Activation by a Four-Membered Heterocyclic Phosphane-Borane Adduct", Chem. Commun., 2007, p. 5072-5074.

(Continued)

Primary Examiner — Porfirio Nazario Gonzalez
(74) Attorney, Agent, or Firm — Lowenstein Sandler PC

(57) ABSTRACT

A compound having the formula (I) where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{20}$ linear alkyl-, RO—, —NRR', —PRR', —SR, fluoro substituted forms thereof, and perfluoro forms thereof: and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, fluoro substituted forms thereof, and perfluoro forms thereof; where R and R' are each independently $C_6$-$C_{18}$aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullify; and M is B, Al, Ga or In.

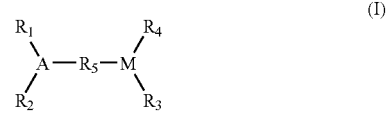

(I)

62 Claims, No Drawings

OTHER PUBLICATIONS

International Search Report for International Patent Application No. PCT/IB2007/004577 issued Nov. 17, 2008.

European Search Report for European Patent Application No. 07 873 357.3 issued Feb. 17, 2012.

Yang, J., et al., "Metal-Free, Organocatalytic Asymmetric Transfer Hydrogenation of α, β-Unsaturated Aldehydes", Angew. Chem. Int. Ed. 2005, 44, 108-110.

Kimura, T., et al., "Novel Metal-Free Hydrogenation of the Carbon-Carbon Double Bond in Azulenoid Enones by Use of Cycloheptatriene and Protic Acid", Organic Letters, 2006, 8(14), 3137-3139.

Chase, P., "Lewis Acid-Catalyzed Hydrogenation: B(C6F5)3-Mediated Reduction of Imines and Nitriles with H2", ChemComm., 2008, 1701-1703.

* cited by examiner

FRUSTRATED LEWIS PAIR COMPOSITIONS

CROSS-REFERENCE TO RELATED APPLICATION

This application claims priority benefit of U.S. Provisional Applications 60/865,684 filed Nov. 14, 2006; and 60/896,557 filed Mar. 23, 2007 the contents of which are hereby incorporated by reference.

FIELD OF THE INVENTION

The present invention in general relates to compounds and compositions capable of splitting dihydrogen, and in particular to compounds and compositions dissociating dihydrogen and use of said compounds in metal-free hydrogenation. These species are also capable of transfer hydrogenation.

BACKGROUND OF THE INVENTION

The generation and use of molecular hydrogen ($H_2$) are important processes to fundamental chemical transformations and biological functions. The overwhelming majority of systems known to either liberate or react with $H_2$ involve reaction at a transition metal center. Hydrogenase enzymes, as well as a plethora of synthetic stoichiometric and catalytic reagents for hydrogenation reactions, are based on the processes of oxidative addition and reductive elimination of $H_2$ at a metal center. Metal-free systems that either react with or liberate $H_2$ are rare. A unique metal-free hydrogenase from methanogenic archaeas has been shown to catalyze reactions with $H_2$, and theoretical studies suggest the role of a folate-like cofactor in the reversible activation/liberation of $H_2$. Several metal-free systems have been shown to activate $H_2$. For example, main group element-$H_2$ reactions in low temperature matrices are also known.

Hydrogenation is the addition of hydrogen to unsaturated organic compounds. Such reactions are used for the production of a myriad of chemical products worldwide, from large-scale operations including the upgrading of crude oil and the production of bulk commodity materials to the synthesis of a variety of fine chemicals used in the food, agricultural, and pharmaceutical industries. The process of hydrogen addition to unsaturated precursors is mediated by either homogeneous or heterogeneous transition metal based catalysts. In the 1960s, the advent of organometallic chemistry gave rise to homogeneous transition metal based hydrogenation catalysts for a variety of substrates. The operation of these catalysts hinges on the key step of oxidative addition of hydrogen. More recently, transition metal, systems that effect heterolytic cleavage of hydrogen at a metal center have been uncovered. In these cases, a metal hydride is formed with concurrent protonation of an amido ligand.

Non-transition metal catalysts for hydrogenation reactions are all but unknown. KOtBu has been shown to act as a catalyst effecting the addition of $H_2$ to benzophenone under forcing conditions of 200° C. and greater than 100 bar $H_2$. Organocatalysts have been developed for hydrogenations of enones and imines; however, such systems do not employ $H_2$ directly but rather a surrogate such as a Hantzsch ester as the stoichiometric source of hydrogen. The development of non-metal hydrogenation catalysts hinges on the discovery of systems that react cleanly with $H_2$, but few are known. Power and coworkers reported the hydrogenation of $Ge_2$-alkyne analogues to give a mixture of $Ge_2$ and primary germane products. J. W. Yang. M. T. Hechavarria Fonseca, B. List, Angew. Chem. 2004, 116, 6829; Angew. Chem. Int. Ed. 2004, 43, 6660. G. H. Spikes. J. C. Fettinger. P. P. Power, J. Am. Chem. Soc. 2005, 127, 12 232. It should be noted that non-transition metal systems have been shown to effect hydrogenation under more forcing conditions. For example. DeWitt. Ramp and Trapasso demonstrated hydrogenation with $iPr_3B$ under 67 atm (1000 psi) $H_2$ at 220° C. E. J. DeWitt, F. L. Ramp, L. E. Trapasso, J. Am. Chem. Soc. 1961, 83, 4672-4672; F. L. Ramp, E. J. DeWitt, L. E. Trapasso, Org. Chem. 1962, 27, 4368-4372). Similarly. Haenel and coworkers (E. Osthaus, M. W. Haenel, in Coal Science and Technology, Vol. 11 Elsevier, Amsterdam, 1987, pp. 765-768 (Proc. 1987 Intern. Conf. Coal Sci., Eds.: J. A. Moulijn, K. A. Nater, H. A. G. Chermin),; M. Yalpani, R. Köster, M. W. Haenel, Erdoel Kohle, Erdgas. Petrochem. 1990, 43, 344-347; M. W. Haenel, J. Narangerel, U.-B. Richter, A. Rufinska, Angew. Chem. 2006, 118, 1077-1082; Angew. Chem. Int. Ed. 2006, 45, 1061-1066; M. W. Haenel, J. Narangerel, U.-B. Richter, A. Rufinska, Prep. Pap. Am. Chem. Soc, Div. Fuel Chem. 2006, 51(2), 741-742) among others showed hydrogenation of coal under almost 15 MPa and 280-350° C. using $BI_3$ or alkyl boranes. M. Yalpani, T. Lunow, R. Köster, Chem. Ber. 1989, 122, 687-693; (b) M. Yalpani, R. Köster, Chem. Per. 1990, 123, 719-724. As well, superacid systems have also been shown to effect hydrogenation of alkenes using $H_2$ pressures of at least 35 atm. M. Siskin, J. Am, Chem. Soc. 1974, 96, 3641; (b) J. Wristers, J. Am. Chem. Soc. 1975, 97, 4312.

The ability to dissociate dihydrogen represents a reaction of considerable importance in fields including hydrogenation of ethenically unsaturated feed stocks, chemical fuel storage, hydrogen purification, and hydrogen getters that prevent hydrogen levels from building beyond a preselected threshold. Traditionally, dihydrogen dissociation has involved the use of metal catalysts and in particular palladium. Conventional catalysts inclusive of metal have a number of limitations that include high material cost, high density, the heterogeneous nature of such catalysts relative to liquid phase reactants, and contamination of resultant products with metal catalysts.

Thus, there exists a need for a hydrogen dissociation catalyst that is independent of metal. Additionally, a catalyst capable of operating as a homogeneous catalyst would afford considerable operational advantages. Further, these hydrogen catalysts operate efficiently at lower or comparable temperatures to those used for existing metal based hydrogenation catalysts.

SUMMARY OF THE INVENTION

A compound is provided that is operative as a hydrogenation catalyst. The compound is capable of homogenous liquid phase catalysis exclusive of a noble metal. A compound has the formula:

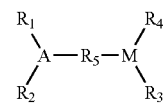

I where each of $R_1$, $R_2$, $R_3$ and $R_4$ is independently $C_6$-$C_{18}$ is aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ is aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent. $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; and M is B, Al, Ga or In.

A composition operative as a hydrogenation catalyst includes a compound having the formula:

II where each of $R_1$ and $R_2$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent. $C_4$-$C_{20}$ branched alkyl-, $C_{16}$-$C_{30}$ linear alkyl-, RO—, —NRR', —PRR', —SR, fluoro substituted forms thereof, and perfluoro forms thereof; $R_6$ is $C_1$-$C_{30}$ alkyl-, $C_6$-$C_{18}$ aryl-, $C_5$-$C_8$ cycloalkyl-, RO—, —NRR', —PRR', —SR, a fluoro substituted form thereof, a perfluoro substituted form thereof, H or F; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; in fluid communication with a composition having the formula:

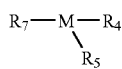

III where each of $R_4$, $R_5$ and $R_7$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms (hereof and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and M is B, Al, Ga or In; or a composition of the formula:

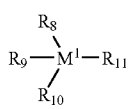

V where $M^1$ is Ti, Zr or Hf; each of $R_8$, $R_9$ and $R_{10}$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, amide, alkoxide, phenoxide, phosphinimide, cyclopentadienyl, indenyl, fluorenyl derivatives, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and $R_{11}$ is $C_1$-$C_{20}$ alkyl linear or branched with the proviso that $R_{11}$ is a better leaving group than any of $R_8$, $R_9$ or $R_{10}$ under nucleophic attack by a hydrogen or other alkyl abstracting agents to yield a cationic $M^1$ species.

A compound is also provided that is an addition reaction product of a compound of formula I and dihydrogen ($H_2$). The compound has the formula:

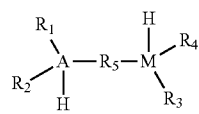

IV where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, fluoro substituted forms thereof and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullity; and M is B, Al, Ga or In.

A process of catalytic hydrogenation of a substrate comprising: independently compound I, a mixture of II and III, compound III, a mixture of II, III-V, compound IV, or compound VI together with dihydrogen and solvent form a catalyst whereby hydrogenation of a substrate is effected.

DETAILED DESCRIPTION OF THE PREFERRED EMBODIMENTS

The present invention has utility as compounds and compositions capable of dissociating dihydrogen and reversibly binding hydrogen atoms. In addition to dihydrogen dissociation, a sacrificial dihydrogen source such as primary or secondary amines, primary or secondary phosphines, alcohols and thiols are also is operative according to the present invention to reduce substrates. According to the present invention, a compound is provided that is the reaction product of a sterically hindered Lewis acid with a sterically hindered Lewis base via an intermediate linker group therebetween.

The prototypical form of an inventive compound I is a reaction product of linker separated sterically hindered phosphine and a sterically hindered borane. An inventive compound has the formula:

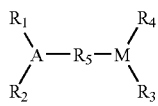
I where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; and M is B, Al, Ga or In.

A bimolecular composition according to the present invention capable of dissociating hydrogen and reversibly binding hydrogen atoms includes in a mixture of a phosphine and a borane incapable of reaction owing to steric hindrance. Sterically hindered phosphine is readily replaced with a nitrogen, oxygen, or sulfur analog as shown in formula II. Sterically hindered borane is readily replaced with an aluminum, gallium, or indium analog as shown in formula III. Lesser sterically hindered systems exhibit reactivity at temperatures dependent on the nature of the compounds. The mixture of sterically hindered Lewis base and Lewis acid compounds operative herein have the formulae II and III, respectively:

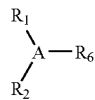
II where each of $R_1$ and $R_2$ is independently $C_6$-$C_{18}$ is aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; $R_6$ is $C_1$-$C_{30}$ alkyl-, $C_6$-$C_{18}$ aryl-, $C_5$-$C_8$ cycloalkyl-, RO—, —NRR', —PRR', —SR, a fluoro substituted form thereof, a perfluoro substituted form thereof, H or F; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity.

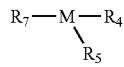
III where each of $R_4$, $R_5$ and $R_7$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and M is B, Al, Ga or In. In a particular embodiment a sterically hindered perfluorinated composition of formula III has hydrogen catalytic activity independent of the presence of a compound of formula II.

A compound of the formula is also provided that is reversibly converted into the compound of formula I through loss of two hydrogen atoms. The compound has the formula:

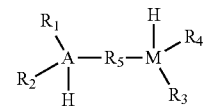
IV where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_3$-$C_{20}$ branched alkyl-, $C_2$-$C_{30}$ linear alkyl-, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullity; and M is B, Al, Ga or In.

In an alternate embodiment, hydrogenation occurs through the interaction of a composition of formula II with a transition metal cation of Ti, Zr, or Hf when A is P or N. The transition metal cation is generated in situ by alkyl group abstraction from an organometallic composition of the formula:

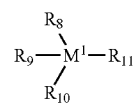
V where $M^1$ is Ti, Zr or Hf; each of $R_8$, $R_9$ and $R_{10}$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, amide, alkoxide, phenoxide, phosphinimide, cyclopentadienyl, indenyl, fluorenyl derivatives, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and $R_{11}$ is $C_1$-$C_{20}$ alkyl linear or branched with the proviso that $R_{11}$ is a better leaving group than any of $R_8$, $R_9$ or $R_{10}$ under nucleophic attack by a hydrogen or other alkyl abstracting agents to yield a cationic $M^1$ species.

The present invention compounds and mixtures of compounds are effective as hydrogenation catalysts for performing reactions illustratively including those provided in Table 1. The compositions and compounds of formulae I-V are operative in hydrogenation catalysis in a neat liquid substrate, in a solution containing substrate, or applied as coating on an inert support.

TABLE 1

Substrate hydrogenation to products according to the present invention.

| Substrates | Products |
| --- | --- |
| ketimines | amines |
| ketene-imines | amines |
| aldimines | amines |
| nitriles | amines |
| aziridines | amines |
| olefins | hydrocarbon |
| ketones | alcohols |
| aldehydes | alcohols |
| borazines | borane-amine adducts |
| acetylene | hydrocarbon |
| enols | alcohols |
| enamines | amines |
| ketenes | alcohol |
| allenes | alkanes |
| esters | alcohols |
| epoxides | alcohols |
| isocyanides | amines |
| lactones | diols |

The present invention is further detailed with respect to the following nonlimiting examples.

EXAMPLE 1

General Catalysis Procedure

The catalyst (0.1-20 mol %) is weighed into a 50 ml round bottomed Schlenk flask and slurried in toluene (2 ml). The reaction is charged with $H_2$. The slurry is then allowed to equilibrate at the desired temperature under an atmosphere of $H_2$ with rapid stirring. A solution of substrate (1.0 mmol) in toluene (2 ml) is added via syringe. Reaction time and temperature vary with substrate. In all cases, the crude mixtures of the completed reactions are pure to the limits of NMR spectroscopy. The product is purified by all volatiles being removed in vacuo trap to trap vacuum distillation or filtration, through a small plug of silica to remove residual catalyst.

EXAMPLE 2

Conversion of N-benzylidine-tert-butyl amine to benzyl-tert-butylamine with $tBu_2PH$—$C_6F_4$—$BH(C_6F_5)_2$ In a glove box, $tBu_2PH$—$C_6F_4$—$BH(C_6F_5)_2$ (0.033 g, 0.05 mmol) is weighed into a 50 ml round bottomed Schlenk flask equipped with a small stir bar and slurried in toluene (2 ml). The reaction is attached to a vacuum/$H_2$ line and freeze-pump-thaw cycled three times. The slurry is then allowed to equilibrate at 80° C. under an atmosphere of $H_2$ with rapid (500 rpm) stirring. A solution of N-benzylidine-tert-butyl amine (0.161 g, 1.0 mmol) in toluene (2 ml) is added via syringe. The reaction is periodically monitored by thin layer chromatography (silica, eluent: 1:5 ethyl acetate/hexanes) and $^1H$ NMR spectroscopy and is complete in 1 hour. The solvent is removed in vacuo and the product benzyl-tert-butylamine is purified by trap to trap vacuum distillation. Isolated yield 0.128 g (79%).

EXAMPLE 3

Alternate General Catalysis Procedure

The catalyst (0.01-0.20 mmol) and substrate (1 mmol) are weighed into a 100 ml round bottomed glass flask equipped with a Kontes valve. Solvent (4 ml) is added, the reaction transferred to a vacuum/$H_2$ line and the mixture is freeze-pump-thaw cycled three times. The mixture is cooled to −196° C. (liquid $N_2$) and 1 atm. $H_2$ is introduced. The flask is sealed, the reaction is placed in a preheated bath and rapidly stirred. Reaction time and temperature vary with substrate. In all cases, the crude reaction mixtures are of the completed reactions are pure to the limits of NMR spectroscopy. The product is purified by removal of all volatiles in vacuo and trap to trap vacuum distillation or nitration through a small plug of silica to remove residual catalyst.

EXAMPLE 4

Conversion of cis-1,2,3-triphenylaziridine to N-1,2 diphenylethyl-N-phenyl amine with $tBu_2PH(C_6F_4)BH(C_6F_5)_2$ In a glove box, $tBu_2PH(C_6F_4)BH(C_6F_5)_2$ (0.33 g, 0.05 mmol) and cis-1.2.3-triphenylaziridine (0.271 g, 1.0 mmol) were weighed into a 100 ml round bottomed glass flask equipped with a Kontes valve and a magnetic stirbar. Toluene (4 ml) is added, the reaction transferred to a vacuum/$H_2$ line and the mixture is freeze-pump-thaw cycled three times. The mixture is cooled to −196° C. (liquid $N_2$) and 1 atm. $H_2$ is introduced. The flask is sealed, the reaction is placed in a 120° C. preheated bath and rapidly (500 rpm) stirred. The reaction is periodically monitored by $^1H$ NMR spectroscopy and is complete in 2 hours. The reaction mixture is poured onto a small plug of silica and eluted with 2:1 hexanes/ethyl acetate (50 ml). The solvent is removed in vacuo and the product N-1,2-diphenylethyl-N-phenyl amine isolated. Yield: 0.269 g (98%)

COMPARATIVE EXAMPLE $B(C_6F_5)_3$-only Reductive Catalysis

In the glovebox, a substrate (1 mmol) per Table 2, $B(C_6F_5)_3$ (26 mg, 0.05 mmol, 5 mol %) and dry toluene (4 ml) are weighed into a 100 ml round bottomed flask equipped with a scalable Teflon tap and small magnetic stirbar. The reaction is then attached to a double manifold $H_2$/vacuum line and degassed (freeze-pump-thaw cyclex3). The reaction is cooled to −196° C. (liquid $N_2$) and 1 atm. $H_2$ is introduced. The flask is sealed and warmed to room temperature. The reaction is then placed in an oil bath heated to the desired temperature and stirred at 500 rpm. At 120° C., the $H_2$ pressure is ~5 atm.

Aliquots are obtained at periodic intervals by rapidly cooling the reaction in a water bath and venting the $H_2$ pressure. Samples are taken by pipette in the glove box. The reaction is re-pressurized using the above procedure. Upon full conversion, the reaction is poured onto a 10 cm plug of silica (200 mesh) and eluted with 2:1 hexanes/ethyl acetate (200 ml). If the amine is not fully soluble in the reaction mixture or the hexanes/ethyl acetate solvent, $CH_2Cl_2$ (3×5 ml) is used to wash the reaction vessel. The collected solvent is removed in vacuo to obtain the product in the time and yield shown in Table 2.

TABLE 2

$B(C_6F_5)_3$-only catalyzed reductions.
Conditions: 120° C., toluene, ~5 atm. $H_2$, 500 rpm stir rate.

subtrate $\xrightarrow{5 \text{ mol \%} B(C_6F_5)_3}$ product

| substrate | time | isolated yield | product |
|---|---|---|---|
| tBu-N=CH-Ph | 2 h[a] | 89% | tBu-NH-CH2-Ph |
| Ph2CH-N=CH-Ph | 1 h | 99% | Ph2CH-NH-CH2-Ph |
| PhSO2-N=CH-Ph | 41 h | 94% | PhSO2-NH-CH2-Ph |
| tBu-N=CPh-Ph | 1 h | 98% | tBu-NH-CHPh-Ph |
| Dipp-N=CMe-Ph | 8 h | 94% | Dipp-NH-CHMe-Ph |

TABLE 2-continued $B(C_6F_5)_3$-only catalyzed reductions.
Conditions: 120° C., toluene, ~5 atm. $H_2$, 500 rpm stir rate.

subtrate $\xrightarrow{5 \text{ mol \%} B(C_6F_5)_3}$ product

| substrate | time | isolated yield | product |
|---|---|---|---|
| Dipp-N=C(tBu)Me | 48 h | 0% | Dipp-NH-CH(tBu)Me |
| Ph-aziridine-Ph (N-Ph) | 2 h | 95% | Ph-CH(NHPh)-CHPh |

[a]conditions, 1 atm. $H_2$, 80° C.

2,6-diisopropylphenyl = Dipp

EXAMPLE 5

$B(C_6F_5)_3$ and Phosphine Reductive Catalysis

In the glovebox, a substrate (1 mmol) per Table 3, is reacted in the presence of $P(2,4,6-Me_3C_6H_2)_3$ (19 mg 0.05 mmol, 5 mol %) or $PtBu_3$, (10 mg, 0.05 mmol, 5 mol %) according to the procedure of the Comparative Example. As shown in Table 3, more efficient reaction with the sterically hindered phosphine (formula II) is noted for the imine $PhCH(N)SO_2Ph$ and $MeCN-B(C_6F_5)_3$ reacts when no reductive catalysis is noted absent the phosphine (formula II).

TABLE 3

Comparison of $B(C_6F_5)_3$-only and $B(C_6F_5)_3$/PMes$_3$ catalyzed reductions.
Conditions: 120° C., toluene, ~5 atm. $H_2$, 500 rpm stir rate.

substrate $\xrightarrow[\text{phosphine}]{5 \text{ mol \%} B(C_6F_5)_3}$ product

| substrate | phosphine (mol %) | time | isolated yield | product |
|---|---|---|---|---|
| PhSO2-N=CH-Ph | — | 41 h | 94% | PhSO2-NH-CH2-Ph |
| | PMes3 (5) | 8 h | 98% | |
| Me-C≡N-B(C6F5)3 | — | 48 h | 0% | Me-CH2-NH2-B(C6H5)3 |
| | PMes3 (5) | 49 h | 91% | |

TABLE 3-continued

Comparison of $B(C_6F_5)_3$-only and $B(C_6F_5)_3$/PMes$_3$ catalyzed reductions.
Conditions: 120° C., toluene, ~5 atm. H$_2$, 500 rpm stir rate.

$$\text{substrate} \xrightarrow[\text{phosphine}]{\frac{5 \text{ mol \%}}{B(C_6F_5)_3}} \text{product}$$

| substrate | phosphine (mol %) | time | isolated yield | product |
|---|---|---|---|---|

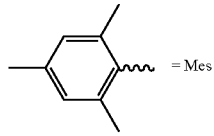

= Mes

EXAMPLE 6

Imine and Nitrile Reduction

In a glove box, a 100 ml glass bomb equipped with a small stir bar and a Teflon screw tap is charged with imine (1 mmol), catalyst (0.05 mmol, 5 mol %), and dry toluene (4 ml). The reaction is transferred to the vacuum/H$_2$ line and is degassed three times with a freeze-pump-thaw cycle. The reaction flask is cooled to −196° C., 1 atm of H$_2$ is introduced, and the flask then sealed and warmed to room temperature. The reaction is placed in a preheated oil bath and stirred at 500 rpm; at 120° C. this gave an H$_2$ pressure of about 5 atm. To take aliquots, the reaction is cooled rapidly in an ice bath, vented to release the H$_2$ pressure, and taken into a glove box. For the catalyst $(2,4,6\text{-Me}_3C_6H_2)_2 \text{PH}(C_6H_4) \text{BH}(C_6F_5)_2$ (denoted as compound 1) and $(\text{tert-butyl})_2 \text{PH}(C_6H_4) \text{BH}(C_6F_5)_2$ (denoted as compound 2), the following products are obtained in the time and yield shown in Table 4.

TABLE 4

Imine and nitrile reduction by catalyst compositions 1 and 2.

| Entry | Substrate | Catalyst | T [8 C.] | t [h] | Yield [%] | Product |
|---|---|---|---|---|---|---|
| 1 | Ph(H)C=NtBu | 1[b] | 80 | 1 | 79 | PhCH$_2$NHtBu |
| 2 | Ph(H)C=NtBu | 2[b] | 80 | 1 | 98 | PhCH$_2$NHtBu |
| 3 | Ph(H)C=NSO$_2$Ph | 1 | 120 | 10.5 | 97 | PhCH$_2$NHSO$_2$Ph |
| 4 | Ph(H)C=NSO$_2$Ph | 2 | 120 | 16 | 87 | PhCH$_2$NHSO$_2$Ph |
| 5 | Ph(H)C=NCHPh$_2$ | 1 | 140 | 1 | 88 | PhPhCH$_2$NHCHPh$_2$ |
| 6 | Ph(H)C=NCH$_2$Ph | 1 | 120 | 48 | 5[c] | PhCH$_2$NHCH$_2$Ph |
| 7 | Ph(H)C=NCH$_2$Ph(B(C$_6$F$_5$)$_3$) | 1 | 120 | 46 | 57 | PhCH$_2$NHCH$_2$Ph(B(C$_6$F$_5$)$_3$) |
| 8 | MeCNB(C$_6$F$_5$)$_3$ | 1 | 120 | 24 | 75 | MeCH$_2$NH$_2$B(C$_6$F$_5$)$_3$ |
| 9 | PhCNB(C$_6$F$_5$)$_3$ | 1 | 120 | 24 | 84 | PhCH$_2$NH$_2$B(C$_6$F$_5$)$_3$ |
| 10 | (CH$_2$CH$_2$CNB(C$_6$F$_5$)$_3$)$_2$ | 1[d] | 120 | 48 | 99 | (CH$_2$CH$_2$CH$_2$NH$_2$B(C$_6$F$_5$)$_3$)$_2$ |
| 11 | PhCHCHPhNPh | 1[d] | 120 | 1.5 | 98 | PhCH$_2$CHPhNHPh |

[a]Standard conditions: 5 mol % catalyst, 4 mL toluene, ca. 5 atm H$_2$.

[b]1 atm H$_2$.

[c]Determined by 1H NMR spectroscopy.

[d]10 mol % catalyst.

EXAMPLE 7

Synthesis of [R$_3$P(C$_6$F$_4$)BF(C$_6$F$_5$)$_2$] R=isopropyl (denoted as compound 3), R=cyclohexyl (denoted as compound 4), of [R$_2$PH(C$_6$F$_4$)BF(C$_6$F$_5$)$_2$] R=tert-butyl (denoted as compound 5) and (2,4,6-Me$_3$C$_6$H$_2$) (denoted as compound 6)

These compounds are prepared in a similar fashion. A clear yellow solution of B(C$_6$F$_5$)$_3$ (0.500 g, 0.98 mmol) and i-Pr$_3$P (0.156 g, 0.98 mmol) or molar equivalent of (C$_6$H$_{11}$)$_3$P, (t-Bu)$_3$ P, or (2,4,6-Me$_3$C$_6$H$_2$)$_3$P in toluene (20 mL) is allowed to stir for 12 h at 25° C. during which time a white precipitate formed. Pentane (10 mL) is added, the mixture filtered and dried in vacuo for 1 h. In the instance of (2,4,6-Me$_3$C$_6$H$_2$)$_3$P stirring took place in refluxing toluene. The product is collected as a white solid.

EXAMPLE 8

Synthesis of [R$_3$P(C$_6$F$_4$)BH(C$_6$F$_5$)$_2$] R=isopropyl (denoted as compound 7), R=cyclohexyl (denoted as compound 8), of [R$_2$PH(C$_6$F$_4$)BH(C$_6$F$_5$)$_2$] R=t-Bu (denoted as compound 9), and (2,4,6-Me$_3$C$_6$H$_2$) (denoted as compound 10)

To a solution of compound 3 (0.400 g, 0.600 mmol) or a molar equivalent of compounds 4, 5 or 6 dissolved in CH$_2$Cl$_2$ (10 mL) is added (CH$_3$)$_2$SiHCl (0.66 mL, 6.00 mmol) via syringe. The reaction is allowed to stir 12 h, during which time a precipitate forms. All volatiles are removed in vacuo to give the product as a white solid.

EXAMPLE 9

Synthesis of [R$_3$P(C$_6$F$_4$)B(C$_6$F$_5$)$_2$][B(C$_6$F$_5$)$_4$] R=isopropyl (denoted as compound 11), R=cyclohexyl (denoted as compound 12), of [R$_2$PH(C$_6$F$_4$)B(C$_6$F$_5$)$_2$][B(C$_6$F$_5$)$_4$] R=t-Bu (denoted as compound 13), (2,4,6-Me$_3$C$_6$H$_2$) (denoted as compound 14)

An orange solution of [Ph$_3$C][B(C$_6$F$_5$)$_4$] (0.420 g, 0.456 mmol) in CH$_2$Cl$_2$ (2 mL) is added to a slurry of compound 7 (0.300 g, 0.457 mmol) or molar equivalent of 8, 9, or 10 in CH$_2$Cl$_2$ (5 mL) to give a faint yellow solution. The reaction is allowed to stir for 30 min and the volatiles are removed in vacuo. Pentane (5 mL) is added and the mixture filtered and washed with toluene (2 mL) and pentane (3×2 mL) to give an off white solid.

EXAMPLE 10

Synthesis of R$_2$P(C$_6$F$_4$)B(C$_6$F$_5$)$_2$ R=tert-butyl (denoted as compound 15), (2,4,6-Me$_3$C$_6$H$_2$) (denoted as compound 16)

A 20 mL vial is charged with compound 5 (0.099 g, 0.150 mmol) or a molar equivalent of composition 6, toluene (10 mL) and diethyl ether (1 mL), forming a white slurry. The mixture is cooled to −35° C. and 3.0 M MeMgBr in diethyl ether (0.060 mL, 0.180 mmol) is added via syringe. Immediate formation of a clear yellow solution is observed. The reaction is allowed to warm to room temperature and stirred for 12 h. All volatiles are removed in vacuo and the product extracted with hexanes (3×5 mL) and filtered through celite. The solvent is removed in vacuo to give a yellow solid.

EXAMPLE 13

Conversion of cis-1,2,3-triphenylaziridine to N-1,2-diphenylethyl-N-phenyl amine with B(C6F5)3 and (2,4,6-Me$_3$C$_6$H$_2$)$_3$P In a glovebox, cis-1,2,3-triphenylaziridine (1 mmol), B(C$_6$F$_5$)$_3$ (6.05 mmol) and (2,4,6-Me$_3$C$_6$H$_2$)$_3$P (0.05 mmol) are reacted according to the procedure of the Comparative Example to yield N-1,2-diphenylethyl-N-phenyl amine.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description, is illustrative of particular embodiments of the invention, but is not meant to be a limitation upon the practice thereof. The following claims, including all equivalents thereof, are intended to define the scope of the invention.

The invention claimed is:

1. A compound comprising:
   a sterically hindered Lewis acid comprising B, Al, Ga, In, Ti, Zr or Hf;
   a sterically hindered Lewis base comprising N, P, S, or O; and
   an intermediate linker group therebetween.

2. A compound of formula I or formula IV

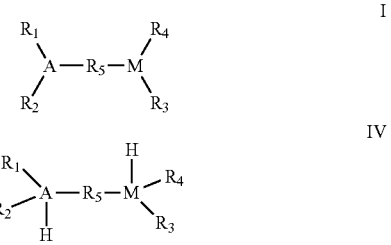

where
  R$_1$, R$_2$, R$_3$ and R$_4$ are, independently: C$_6$-C$_{18}$ aryl; C$_5$-C$_8$ cycloalkyl; C$_6$-C$_{18}$ aryl having at least one C$_1$-C$_{20}$ alkyl substituent; C$_5$-C$_8$ cycloalkyl having at least one C$_1$-C$_{20}$ alkyl substituent; C$_4$-C$_{20}$ branched alkyl; C$_{16}$-C$_{30}$ linear alkyl; —OR; —NRR'; —PRR'; or —SR;
  R$_5$ is: C$_6$-C$_{18}$ arylene; C$_5$-C$_8$ cycloalkanediyl; C$_6$-C$_{18}$ arylene having at least one C$_1$-C$_{20}$ alkyl substituent; C$_5$-C$_8$ cycloalkanediyl having at least one C$_1$-C$_{20}$ alkyl substituent; C$_3$-C$_{20}$ branched alkanediyl; or C$_2$-C$_{30}$ linear alkanediyl;
  R and R' are, independently: C$_6$-C$_{18}$ aryl; C$_5$-C$_8$ cycloalkyl; C$_6$-C$_{18}$ aryl having at least one C$_1$-C$_{20}$ alkyl substituent; C$_5$-C$_8$ cycloalkyl having at least one C$_1$-C$_{20}$ alkyl substituent; C$_4$-C$_{20}$ branched alkyl; or C$_2$-C$_{30}$ linear alkyl;
  A is: N; P; S; or O; with the proviso that when A is S or O, R$_2$ is a nullity; and
  M is: B; Al; Ga; or In.

3. The compound of claim 2, wherein one or more of R$_1$, R$_2$, R$_3$, R$_4$, R$_5$, R, and R' are independently substituted.

4. The compound of claim 3, wherein substituted is fluoro substituted.

5. The compound of claim 3, wherein substituted is perfluoro substituted.

6. The compound of claim 2, wherein A comprises phosphorus.

7. The compound of claim 2, wherein M comprises boron.

8. The compound of claim 2, wherein $R_5$ is $C_6$-$C_{18}$ arylene.

9. The compound of claim 2, wherein at least one of $R_1$ and $R_2$ is $C_6$-$C_{18}$ aryl.

10. The compound of claim 9, wherein at least one of $C_6$-$C_{18}$ aryl is fluorosubstituted.

11. The compound of claim 2, wherein at least one of $R_3$ and $R_4$ is $C_6$-$C_{18}$ aryl or $C_4$-$C_{20}$ branched alkyl.

12. The compound of claim 11, wherein at least one of $R_3$ and $R_4$ is fluorosubstituted.

13. The compound of claim 11, wherein at least one of $R_3$ and $R_4$ is perfluoro substituted.

14. The compound of claim 2, wherein $R_1$ and $R_2$ are 2,4,6-$(CH_3)_3C_6H_2$.

15. The compound of claim 2, wherein $R_5$ is perfluorinated.

16. (Tert-butyl)$_2$P($C_6F_4$)B($C_6F_5$)$_2$ ("compound 15") or (2,4,6-Me$_3C_6H_2$)$_2$P($C_6F_4$)B($C_6F_5$)$_2$ ("compound 16").

17. (2,4,6-Me$_3C_6H_2$)$_2$PH($C_6H_4$)BH($C_6F_5$)$_2$ ("compound 1").

18. (tert-butyl)$_2$PH($C_6H_4$)BH($C_6F_5$)$_2$ ("compound 2").

19. A process comprising dissociating an addition reaction reagent by combining the reagent and:
    (i) a compound of formula I;
    (ii) a compound of formula IV;
    (iii) a mixture of a compound of formula II in fluid communication with a compound of formula III; or
    (iv) a compound of formula III, to form a catalyst,
wherein the compounds of formula I and IV are

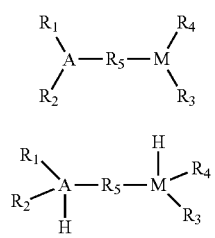

where
   $R_1$, $R_2$, $R_3$ and $R_4$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
   $R_5$ is: $C_6$-$C_{18}$ arylene; $C_5$-$C_8$ cycloalkanediyl; $C_6$-$C_{18}$ arylene having at least one $C_1$-$C_{20}$ alkyl substituent; $C_5$-$C_8$ cycloalkanediyl having at least one $C_1$-$C_{20}$ alkyl substituent; $C_3$-$C_{20}$ branched alkanediyl; or $C_2$-$C_{30}$ linear alkanediyl;
   R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl;
   A is: N; P; S; or O; with the proviso that when A is S or O, $R_2$ is a nullity; and
   M is: B; Al; Ga; or In,
and wherein the compounds of formula II and III are

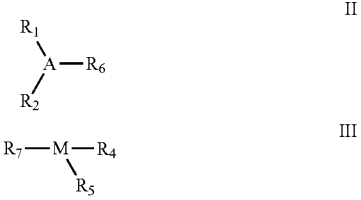

wherein
   $R_1$, $R_2$, $R_4$, $R_5$ and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
   $R_6$ is $C_1$-$C_{30}$ alkyl; $C_6$-$C_{18}$ aryl; $C_5$-$C_8$ cycloalkyl; —OR; —NRR'; —PRR'; —SR; H; or F;
   R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;
   A is N; P; S; or O; with the proviso that when A is S or O, $R_2$ is a nullity; and
   M is B, Al, Ga or In.

20. A process comprising dissociating an addition reaction reagent by combining the reagent and:
    (i) a compound of formula I;
    (ii) a compound of formula IV; or
    (iii) a mixture of a compound of formula II in fluid communication with a compound of formula III, to form a catalyst,
wherein the compounds of formula I and IV are

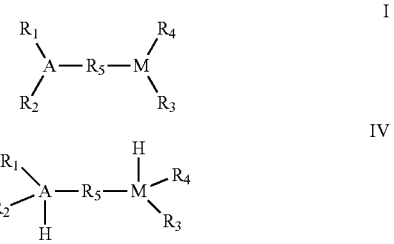

where
   $R_1$, $R_2$, $R_3$ and $R_4$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
   $R_5$ is: $C_6$-$C_{18}$ arylene; $C_5$-$C_8$ cycloalkanediyl; $C_6$-$C_{18}$ arylene having at least one $C_1$-$C_{20}$ alkyl substituent; $C_5$-$C_8$ cycloalkanediyl having at least one $C_1$-$C_{20}$ alkyl substituent; $C_3$-$C_{20}$ branched alkanediyl; or $C_2$-$C_{30}$ linear alkanediyl;
   R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl;

A is: N; P; S; or O; with the proviso that when A is S or O, $R_2$ is a nullity; and M is: B; Al; Ga; or In, and wherein the compounds of formula II and III are

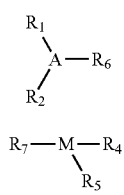

II

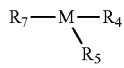

III wherein $R_1$, $R_2$, $R_4$, $R_5$ and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_6$ is $C_1$-$C_{30}$ alkyl; $C_6$-$C_{18}$ aryl; $C_5$-$C_8$ cycloalkyl; —OR; —NRR'; —PRR'; —SR; H; or F;

R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;

A is N; P; S; or O; with the proviso that when A is S or O, $R_2$ is a nullity; and M is B, Al, Ga or In.

21. The process of claim 19, further comprising reacting a substrate and the catalyst to form a reduction product.

22. The process of claim 19, further comprising reacting a substrate so that the substrate undergoes addition of the reagent.

23. The process of claim 19, wherein the reagent is dihydrogen.

24. The process of claim 19, wherein the reagent is a dihydrogen source.

25. The process of claim 24, wherein the dihydrogen source comprises primary amine, secondary amine, primary phosphine, secondary phosphine, alcohol, or thiol.

26. A process comprising:
providing in a reaction vessel a compound or mixture selected from:
a compound of formula I;
a compound of formula III;
a compound of formula IV;
a mixture of a compound of formula II and a compound of formula III;
a mixture of a compound of formula II and a compound of formula I; or
a mixture of a compound of formula II and a compound of formula IV; and
a substrate;
charging the reaction vessel with dihydrogen;
forming a catalyst;
reacting to form a reduction product that is a hydrogenated form of the substrate; and
obtaining the reduction product;

wherein, when the compound or mixture is a compound of formula III, the substrate comprises N, P, S, or O, wherein the compounds of formula I and IV are

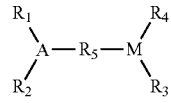

I

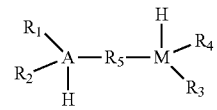

IV where $R_1$, $R_2$, $R_3$ and $R_4$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_5$ is: $C_6$-$C_{18}$ arylene; $C_5$-$C_8$ cycloalkanediyl; $C_6$-$C_{18}$ arylene having at least one $C_1$-$C_{20}$ alkyl substituent; $C_5$-$C_8$ cycloalkanediyl having at least one $C_1$-$C_{20}$ alkyl substituent; $C_3$-$C_{20}$ branched alkanediyl; or $C_2$-$C_{30}$ linear alkanediyl;

R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl;

A is: N; P; S; or O; with the proviso that when A is S or O, $R_2$ is a nullity; and M is: B; Al; Ga; or In, and wherein the compounds of formula II and III are

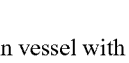

II

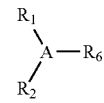

III wherein $R_1$, $R_2$, $R_4$, $R_5$ and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_6$ is $C_1$-$C_{30}$ alkyl; $C_6$-$C_{18}$ aryl; $C_5$-$C_8$ cycloalkyl; —OR; —NRR'; —PRR'; —SR; H; or F;

R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;

A is N; P; S; or O; with the proviso that when A is S or O, $R_2$ is a nullity; and M is B, Al, Ga or In.

27. The process of claim 21, wherein the substrate is a liquid.

28. The process of claim 19, further comprising adding solvent.

29. The process of claim 26, further comprising heating the reaction vessel.

30. The process of claim 26, further comprising placing the reaction vessel under pressure with dihydrogen.

31. The process of claim 19, wherein the compound or mixture is a compound of formula IV.

32. The process of claim 31, wherein the compound of formula IV comprises $(2,4,6\text{-Me}_3C_6H_2)_2PH(C_6H_4)BH(C_6F_5)_2$ ("compound 1").

33. The process of claim 31, wherein the compound of formula IV comprises $(\text{tert-butyl})_2PH(C_6H_4)BH(C_6F_5)_2$ ("compound 2").

34. The process of claim 21, wherein the substrate is Ph(H)C=NtBu.

35. The process of claim 21, wherein the substrate is a substrate of Table 4 and the compound or mixture is a compound of formula IV comprising $(2,4,6\text{-Me}_3C_6H_2)_2PH(C_6H_4)BH(C_6F_5)_2$ ("compound 1"); $(\text{tert-butyl})_2PH(C_6H_4)BH(C_6F_5)_2$ ("compound 2"); or $(\text{tert-butyl})_2PH(C_6F_4)BH(C_6F_5)_2$.

36. The process of claim 21, wherein the compound or mixture is a mixture of a compound of formula II and a compound of formula III; the substrate is a substrate of Table 3; and the product is a product of Table 3.

37. The process of claim 36, wherein the compound of formula II is $(2,4,6\text{-Me}_3C_6H_2)_3P$ and the compound of formula III is $B(C_6F_5)_3$.

38. The process of claim 36, wherein the substrate is cis-1,2,3-triphenylaziridine and the product is N-1,2-diphenyl-ethyl-N-phenyl amine.

39. The process of claim 21, wherein the substrate is a substrate of Table 2; the compound or mixture is a compound of formula III; and the product is a product of Table 2.

40. The process of claim 21, further comprising purifying the product.

41. The process of claim 40, wherein purifying comprises at least one of filtering, distilling, placing under reduced pressure, extracting, or a combination thereof.

42. The process of claim 41, wherein filtering includes filtering though silica or celite.

43. The process of claim 26, wherein the compound of formula III is:
$B(C_6F_5)_3$;
$[(\text{iso-propyl})_3P(C_6F_4)B(C_6F_5)_2][B(C_6F_5)_4]$ ("compound 11");
$[(\text{cyclohexyl})_3P(C_6F_4)B(C_6F_5)_2][B(C_6F_5)_4]$ ("compound 12");
$[(\text{tert-butyl})_2PH(C_6F_4)B(C_6F_5)_2][B(C_6F_5)_4]$ ("compound 13"); or
$[(2,4,6\text{-Me}_3C_6H_2)_2PH(C_6F_4)B(C_6F_5)_2][B(C_6F_5)_4]$ ("compound 14").

44. The process of claim 21, wherein the substrate is a compound of Table 2 or a compound of Table 3.

45. The process of claim 19, wherein the compound or mixture is a mixture of the compound of formula II and the compound of formula III, wherein the compound of formula II is $P(2,4,6\text{-Me}_3C_6H_2)_3$ and the compound of formula III is $B(C_6F_5)_3$.

46. The process of claim 19, wherein the compound of formula III is:
$(\text{tert-butyl})_2PH(C_6F_4)B(C_6F_5)_2][B(C_6F_5)_4]$ ("compound 13"); or
$(2,4,6\text{-Me}_3C_6H_2)_2PH(C_6F_4)B(C_6F_5)_2][B(C_6F_5)_4]$ ("compound 14").

47. The process of claim 21, wherein the substrate and the product that is a reduced form of the substrate are selected from:

| Substrate | Reduction Product |
|---|---|
| Ketimine | Amine |
| Aldimine | Amine |
| Nitrile | Amine |
| Aziridine | Amine |
| Isocyanide | Amine |
| Ketone | Alcohol |
| Aldehyde | Alcohol |
| Enol | Alcohol |
| Ketene | Alcohol |
| Ester | Alcohol |
| Epoxide | Alcohol |
| Allene | Alkane |
| Olefin | Hydrocarbon |
| Acetylene | Hydrocarbon |
| Borazine | Borane-amine adduct; or |
| Lactone | Diol. |

48. The process of claim 47, wherein substrate cis-1,2,3-triphenylaziridine is reduced to N-1,2-diphenylethyl-N-phenylamine.

49. The process of claim 47, wherein substrate N-benzylidine-tert-butylamine is reduced to benzyl-tert-butylamine.

50. The process of claim 47, wherein the substrate is a substrate of Table 2, and the product is a product of Table 2.

51. A process for dissociating dihydrogen and reversibly binding hydrogen atoms to at least one molecule, comprising exposing dihydrogen, under conditions that induce binding, to:
(i) a compound comprising a sterically hindered Lewis acid comprising B, Al, Ga, In, Ti, Zr or Hf; a sterically hindered Lewis base comprising N, P, S, or O; and an intermediate linker group therebetween;
(ii) a compound of formula I;
(iii) a compound of formula IV;
(iv) a composition comprising a first compound comprising a sterically hindered Lewis acid; and a second compound comprising a sterically hindered Lewis base; wherein the Lewis acid comprises B, Al, Ga, In, Ti, Zr or Hf, and wherein the Lewis base comprises N, P, S, or O;
(v) a compound of formula II in fluid communication with a compound of formula III; or
(vi) a compound of formula IIa in fluid communication with a compound of formula V, where the compounds of formula I or formula IV are

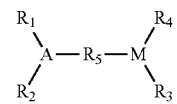

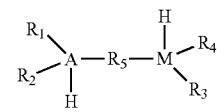

where
$R_1$, $R_2$, $R_3$ and $R_4$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_5$ is: $C_6$-$C_{18}$ arylene; $C_5$-$C_8$ cycloalkanediyl; $C_6$-$C_{18}$ arylene having at least one $C_1$-$C_{20}$ alkyl substituent; $C_5$-$C_8$ cycloalkanediyl having at least one $C_1$-$C_{20}$ alkyl substituent; $C_3$-$C_{20}$ branched alkanediyl; or $C_2$-$C_{30}$ linear alkanediyl;

R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl;

A is: N; P; S; or O; with the proviso that when A is S or O, $R_2$ is a nullity; and M is: B; Al; Ga; or In, where the compounds of formulas II and III are

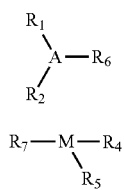

where $R_1$, $R_2$, $R_4$, $R_5$ and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_6$ is $C_1$-$C_{30}$ alkyl; $C_6$-$C_{18}$ aryl; $C_5$-$C_8$ cycloalkyl; —OR; —NRR'; —PRR'; —SR; H; or F;

R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;

A is N; P; S; or O; with the proviso that when A is S or O, $R_2$ is a nullity; and M is B, Al, Ga or In, and where the compounds of formulas IIa and V are

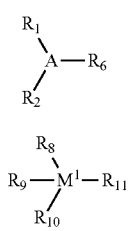

where $R_1$ and $R_2$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;

$R_6$ is $C_1$-$C_{30}$ alkyl; $C_6$-$C_{18}$ aryl; $C_5$-$C_8$ cycloalkyl; —OR; —NRR'; —PRR'; —SR; H; or F;

$R_8$, $R_9$, and $R_{10}$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; amide; alkoxide; phenoxide; phosphinimide; cyclopentadienyl; indenyl; fluorenyl derivatives; —OR; —NRR'; —PRR'; or —SR;

$R_{11}$ is $C_1$-$C_{20}$ alkyl linear or branched with the proviso that $R_{11}$ is a better leaving group than any of $R_8$, $R_9$ or $R_{10}$ under nucleophic attack by a hydrogen or other alkyl abstracting agents to yield a cationic $M^1$ species;

R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;

A is N; P; S; or O; with the proviso that when A is S or O, $R_2$ is a nullity; and $M^1$ is Ti, Zr or Hf.

52. The process of claim 51, wherein conditions that induce binding comprise heat, pressure, or a combination thereof.

53. The process of claim 51 wherein conditions that induce binding comprise heating at 120° C. and placing at about 5 atm pressure using $H_2$.

54. The process of claim 51, further comprising adding solvent.

55. A process for hydrogenating a substrate, comprising:
mixing a compound of claim 1 and a substrate;
charging with dihydrogen; and
reacting to form a reduction product that is a hydrogenated form of the substrate.

56. A process for hydrogenating a substrate, comprising:
mixing a compound of claim 1, a substrate, and a dihydrogen source; and
reacting to form a reduction product that is a hydrogenated form of the substrate.

57. The process of claim 56, wherein the dihydrogen source comprises primary amine, secondary amine, primary phosphine, secondary phosphine, alcohol, or thiol.

58. A process for hydrogenating a substrate, comprising:
mixing in a reaction vessel a compound that comprises a sterically hindered Lewis acid and a substrate that comprises a sterically hindered Lewis base;
charging the reaction vessel with dihydrogen; and
reacting to form a reduction product that is a hydrogenated form of the substrate.

59. The process of claim 58, where the substrate is a liquid.

60. The process of claim 58, further comprising adding solvent.

61. The process of claim 58, further comprising heating the reaction vessel.

62. A process for preparing an addition reaction product of a substrate, comprising catalyzing a reaction of a substrate and an addition reaction reagent by combining the substrate and the addition reaction reagent with:
(i) a compound of formula I;
(ii) a compound of formula IV;

(iii) a mixture of a compound of formula II in fluid communication with a compound of formula III; or
(iv) a compound of formula III,
wherein the compounds of formula I and IV are

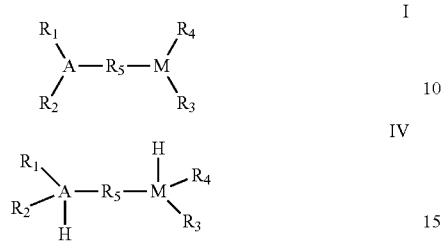

where
- $R_1$, $R_2$, $R_3$ and $R_4$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
- $R_5$ is: $C_6$-$C_{18}$ arylene; $C_5$-$C_8$ cycloalkanediyl; $C_6$-$C_{18}$ arylene having at least one $C_1$-$C_{20}$ alkyl substituent; $C_5$-$C_8$ cycloalkanediyl having at least one $C_1$-$C_{20}$ alkyl substituent; $C_3$-$C_{20}$ branched alkanediyl; or $C_2$-$C_{30}$ linear alkanediyl;
- R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl;
- A is: N; P; S; or O; with the proviso that when A is S or O, $R_2$ is a nullity; and
- M is: B; Al; Ga; or In, and wherein the compounds of formula II and III are

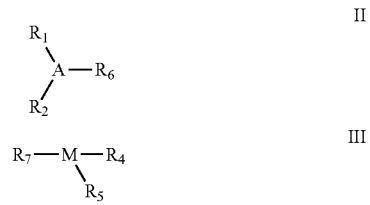

wherein
- $R_1$, $R_2$, $R_4$, $R_5$ and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
- $R_6$ is $C_1$-$C_{30}$ alkyl; $C_6$-$C_{18}$ aryl; $C_5$-$C_8$ cycloalkyl; —OR; —NRR'; —PRR'; —SR; H; or F;
- R and R' are each, independently: $C_6$-$C_{18}$ aryl-; $C_5$-$C_8$ cycloalkyl-; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl-; or $C_2$-$C_{30}$ linear alkyl-;
- A is N; P; S; or O; with the proviso that when A is S or O, $R_2$ is a nullity; and
- M is B, Al, Ga or In.

* * * * *